(12) United States Patent
Sughrue et al.

(10) Patent No.: US 11,961,004 B2
(45) Date of Patent: *Apr. 16, 2024

(54) PREDICTING BRAIN DATA USING MACHINE LEARNING MODELS

(71) Applicant: Omniscient Neurotechnology Pty Limited, Sydney (AU)

(72) Inventors: Michael Edward Sughrue, Sydney (AU); Stephane Philippe Doyen, Glebe (AU); Peter James Nicholas, South Hurstville (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 92 days.

This patent is subject to a terminal disclaimer.

(21) Appl. No.: 17/481,950

(22) Filed: Sep. 22, 2021

(65) Prior Publication Data
US 2022/0222540 A1 Jul. 14, 2022

Related U.S. Application Data

(63) Continuation of application No. 17/145,234, filed on Jan. 8, 2021, now Pat. No. 11,151,456.

(51) Int. Cl.
*G01N 33/48* (2006.01)
*A61B 5/00* (2006.01)
(Continued)

(52) U.S. Cl.
CPC .......... *G06N 3/088* (2013.01); *A61B 5/0042* (2013.01); *A61B 5/055* (2013.01); *A61B 5/369* (2021.01);
(Continued)

(58) Field of Classification Search
CPC ...... G06N 3/088; G06N 3/045; A61B 5/0042; A61B 5/055; A61B 5/369; A61B 5/377;
(Continued)

(56) References Cited

U.S. PATENT DOCUMENTS 8,742,754 B2 6/2014 Hasan
9,747,421 B2 8/2017 Krishna et al.
(Continued)

FOREIGN PATENT DOCUMENTS

WO WO 2001/038895 5/2001
WO WO 2014/153466 9/2014
(Continued)

OTHER PUBLICATIONS

Deligianni et al., "Relating resting-state fMRI and EEG whole-brain connectomes across frequency bands," Frontiers in Neuroscience, 2014, 8(258):1-16.
(Continued)

*Primary Examiner* — Russell S Negin
(74) *Attorney, Agent, or Firm* — Fish & Richardson P.C.

(57) ABSTRACT

Methods, systems, and apparatus, including computer programs encoded on computer storage media, for predicted brain data of a patient. One of the methods includes receiving montage configuration data for a specified montage; receiving raw EEG data captured using the specified montage from a brain of a particular subject; generating, using the montage configuration data and the raw EEG data, EEG connectivity data for the specified montage; using a generative neural network to map the EEG connectivity data to predicted fMRI connectivity data, the generative neural network having been trained using training EEG-fMRI connectivity data pairs, each pair comprising EEG connectivity data of a subject and fMRI connectivity data of the same subject; and taking an action based on the predicted fMRI connectivity data.

18 Claims, 8 Drawing Sheets

(51) Int. Cl.

| | | |
|---|---|---|
| *A61B 5/055* | (2006.01) | |
| *A61B 5/369* | (2021.01) | |
| *A61B 5/377* | (2021.01) | |
| *G01N 33/50* | (2006.01) | |
| *G06N 3/045* | (2023.01) | |
| *G06N 3/088* | (2023.01) | |
| *G16H 20/30* | (2018.01) | |
| *G16H 20/40* | (2018.01) | |
| *G16H 30/20* | (2018.01) | |
| *G16H 30/40* | (2018.01) | |
| *G16H 40/67* | (2018.01) | |
| *G16H 50/20* | (2018.01) | |
| *G16H 50/70* | (2018.01) | |

(52) U.S. Cl.
CPC ............ *A61B 5/377* (2021.01); *A61B 5/7257* (2013.01); *A61B 5/7267* (2013.01); *G06N 3/045* (2023.01); *G16H 20/30* (2018.01); *G16H 20/40* (2018.01); *G16H 30/20* (2018.01); *G16H 30/40* (2018.01); *G16H 40/67* (2018.01); *G16H 50/20* (2018.01); *G16H 50/70* (2018.01)

(58) Field of Classification Search
CPC .... A61B 5/7257; A61B 5/7267; G16H 20/30; G16H 20/40; G16H 30/20; G16H 30/40; G16H 50/20; G16H 50/70
See application file for complete search history.

(56) References Cited

U.S. PATENT DOCUMENTS

| | | | | |
|---|---|---|---|---|
| 11,087,877 | B1 | 8/2021 | Sughrue et al. | |
| 11,151,456 | B1* | 10/2021 | Sughrue | A61B 5/0042 |
| 11,475,276 | B1* | 10/2022 | Shrivastava | G06N 3/08 |
| 11,631,000 | B2* | 4/2023 | Laszlo | G06N 3/006 |
| | | | | 706/15 |
| 2009/0279762 | A1 | 11/2009 | Tsukimoto | |
| 2010/0004527 | A1 | 1/2010 | Dale et al. | |
| 2010/0014727 | A1 | 1/2010 | Hu | |
| 2017/0035320 | A1 | 2/2017 | Verma et al. | |
| 2017/0052241 | A1 | 2/2017 | Cetingul et al. | |
| 2018/0025489 | A1 | 1/2018 | Tiwari et al. | |
| 2018/0173997 | A1 | 6/2018 | Shen et al. | |
| 2019/0166434 | A1 | 5/2019 | Petley et al. | |
| 2020/0337625 | A1 | 10/2020 | Aimone et al. | |
| 2021/0106830 | A1 | 4/2021 | Provenza et al. | |
| 2021/0264623 | A1 | 8/2021 | Tandon et al. | |
| 2021/0369147 | A1 | 12/2021 | Cheung et al. | |
| 2023/0108267 | A1 | 4/2023 | Sughrue et al. | |

FOREIGN PATENT DOCUMENTS

| | | |
|---|---|---|
| WO | WO 2016/083927 | 6/2016 |
| WO | WO 2018/162307 | 9/2018 |
| WO | WO 2019/100032 | 5/2019 |

OTHER PUBLICATIONS

Zhai et al., "A Study on the Reference Electrode Standardization Technique for a Realistic Head Model," Computer Methods and Programs in Biomedicine vol. 76, 2004, p. 229-238.

Coalson et al., "The impact of traditional neuroimaging methods on the spatial localization of cortical areas." Proceedings of the National Academy of Sciences, 2018, 115.27:E6356-65.

Dipy.org [online], "Introduction to Basic Tracking," retrieved on Dec. 2, 2020, retrieved from URL <https://dipy.org/documentation/1.3.0./examples_built/tracking_introduction_eudx/#example-tracking-introduction-eudx?>, 8 pages.

Giacometti et al., "Algorithm to find high density EEG scalp coordinates and analysis of their correspondence to structural and functional regions of the brain," Journal of Neuroscience Methods, vol. 229, pp. 84-96. (Year: 2014).

Huang et al., "Inverse-Transform AutoEncoder for Anomaly Detection" arXiv, 2019, 5(6):1-15.

LaPlante et al., "The Connectome Visualization Utility: Software for Visualization of Human Brain Networks," PLoS One, Dec. 2014, 9((12):1-18.

Liu et al. A convolution neural network for transcoding simultaneously acquired EEG-fMRI data. 9th International IEEE EMBS Conference on Neural Engineering, pp. 477-482. (Year: 2019).

Moreno-Donninguez, "Whole-brain Cortical Parcellation: A Hierarchical Method Based on dMRI Tractography" 2014, Ph.D. Thesis in Engineering, Max Planck Institute for Human Cognitive and Brain Sciences Leipzig, 188 pages.

Najdenovska et al.,"In-vivo probabilistic atlas of human thalamic nuclei based on diffusion-weighted magnetic resonance imaging" Scientific Data, Nov. 2018, 5:180270.

Petrovic et al., "Evaluating Volumetric Brain Registration Performance Using Structural Connectivity Information", 2011, Med. Image Compuy Comput. Assist. Interv., 14(2):524-31.

pypi.org, [online] "DeepDefacer: Automatic Removal of Facial Features via Deep Learning" Jan. 13, 2019, retrieved on Dec. 2, 2020, retrieved from URL <https://pypi.org/project/deepdefacer/>, 4 pages.

Toga et al., "The role of image registration in brain mapping"; Image Vis Comput., Jan. 2001, 19(1-2): 3-24.

Urchs et al., "MIST: A multi-resolution parcellation of functional brain networks," MNI Open Research, Dec. 5, 2017, 1(3):1-30.

Xia et al., "BrainNet Viewer: A Network Visualization Tool for Human Brain Connectomics," PLoS One, Jul. 2013, 8(7):1-15.

Kreitz et al., "A New Analysis of Resting State Connectivity and Graph Theory Reveals Distinctive Short-Term Modulations due to Whisker Stimulation in Rats," Frontiers in Neuroscience, 2018, 12(334): 1-19.

* cited by examiner

PREDICTING BRAIN DATA USING MACHINE LEARNING MODELS

CROSS-REFERENCE TO RELATED APPLICATIONS

This application is a continuation of U.S. application Ser. No. 17/145,234, filed Jan. 8, 2021, contents of which is herein incorporated in its entirety.

This application is related to the U.S. patent application Ser. No. 17/066,171, filed on Oct. 8, 2020, and incorporated herein by reference in its entirety.

This application is also related to the U.S. patent application Ser. No. 17/066,178, filed on Oct. 8, 2020, and incorporated herein by reference in its entirety.

This application is also related to the U.S. Patent Application entitled "Processing Brain Data using Autoencoder Neural Networks," to Michael Sughrue, Stephane Doyen, and Peter Nicholas, filed on Jan. 8, 2021 and incorporated herein by reference in its entirety.

BACKGROUND

This specification relates to processing data related to the brain of a patient, e.g., functional magnetic resonance imaging (fMRI) data and/or tractography data. One can derive brain functional connectivity data from fMRI and tractography data.

Brain functional connectivity data characterizes, for each of one or more pairs of locations within the brain of a patient, the degree to which brain activity in the pair of locations is correlated.

One can gather data related to the brain of the patient by obtaining and processing images of the brain of the patient, e.g., using magnetic resonance imaging (MRI), diffusion tensor imaging (DTI), or functional MRI imaging (fMRI). Diffusion tensor imaging uses magnetic resonance images to measure diffusion of water in a human brain. One can use the measured diffusion to generate tractography data, which can include images of neural tracts and corresponding white matter fibers of the subject brain.

Data related to the brain of a single patient can be highly complex and high-dimensional, and therefore difficult for a clinician to manually inspect and parse, e.g., to plan a surgery or diagnose the patient for a brain disease or mental disorder. For example, a connectivity matrix, e.g., a connectivity matrix of fMRI data, of the brain of a patient can be a matrix with hundreds of thousands or millions of elements.

SUMMARY

This specification relates to generating predicted brain data of a first type using brain data of a second type that has been captured from the brain of the patient. In this specification, "predicted" brain data of a patient is data generated by a computer system characterizing a prediction for a particular type of brain data that might be generated if the particular type of brain data were captured from the brain of patient by one or more sensors. Predicted brain data of a particular type can be generated from brain data of a second type that has been captured from the brain of the patient.

For example, a system can generate predicted fMRI data for a patient using EEG data captured from the brain of the patient. As a particular example, the predicted fMRI data can characterize an fMRI connectivity matrix that represents, for each pair of parcellations in a set of parcellations, the correlation between the brain activity of the pair of parcellations according to fMRI data. The EEG data can characterize an EEG connectivity matrix that represents, for each pair of parcellations in a set of parcellations, the correlation between the brain activity of the pair of parcellations according to the captured EEG data.

In this specification, brain data can be any data characterizing the brain of a patient. For example, brain data can include one or both of i) direct measurement data of the brain of the patient, e.g., images of the brain collected using brain imaging techniques, or ii) data that has been derived or generated from initial measurement data of the brain of the patient, e.g., connectivity matrices.

Particular embodiments of the subject matter described in this specification can be implemented so as to realize one or more of the following advantages.

Some types of brain data are more easily or more inexpensively obtained than other types of brain data. For example, MRI machines can be significantly more expensive than EEG sensors, and therefore clinicians in some communities may not have access to an MRI machine but may have access to an EEG sensor. As a particular example, MRI machines can be prohibitively expensive in the developing world and other underprivileged communities. Using techniques described in this specification, a system can use brain data that is available as a proxy for brain data that is not available, e.g., by using EEG data captured from the brain of a patient to generate predicted fMRI data of the patient.

Furthermore, different types of brain data can have different advantages over each other, and therefore the most useful type of brain data can depend on the particular use case. For example, fMRI data includes rich spatial information but relatively little temporal information, while EEG data includes rich temporal information but relatively little spatial information. Also, some analytical techniques and/or tools exist (or are better developed) for a first type of brain data as compared to a second type of brain data. Using techniques described in this specification, a system can automatically generate predicted brain data of a first type that is preferable, e.g., given the use case, but is not available, using brain data of a second type that is less preferable but is available. The predicted brain data of the first type can encode useful information that was not encoded in the brain data of the second type.

In some implementations described in this specification in which the system processes EEG data to generate predicted fMRI data, the system can process EEG data generated using an EEG sensor that is configured in a way that the system has not seen before, i.e., the system has not been trained using such an EEG sensor configuration. For example, the system can process EEG data generated using an EEG sensor that has a montage that was not included in the training data during training of the system. Thus, the system can receive EEG data as input that corresponds to any montage. In this specification, a montage is a particular configuration of electrodes of an EEG sensor on the scalp of a user.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a system that can generate predicted brain data of a first type for a patient using brain data of a second type captured from the brain of the patient.

Figure 1A:
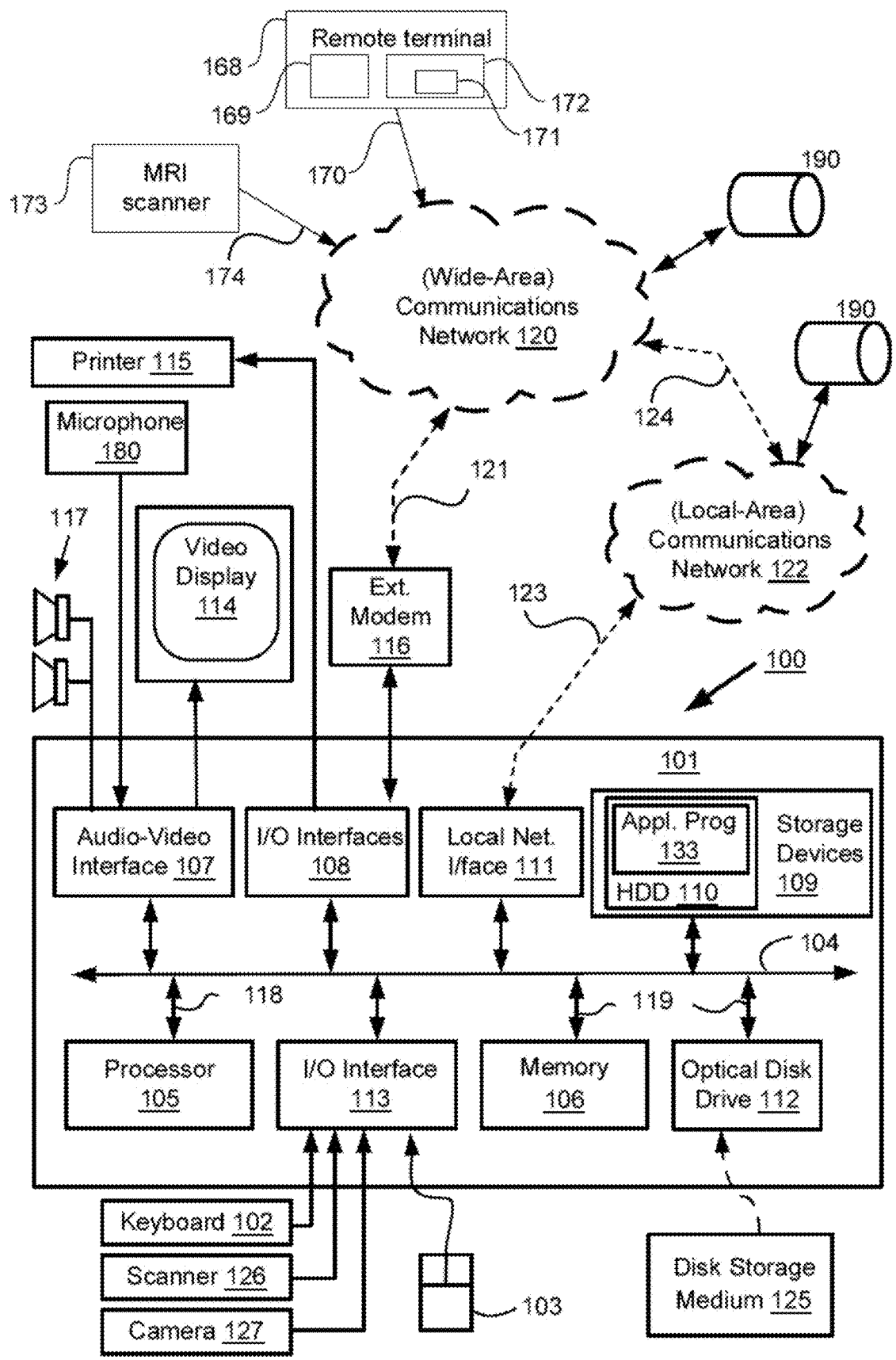
FIG. 1A and FIG. 1B are block diagrams that illustrate an example computer system for use in processing medical images.
Figure 1B:
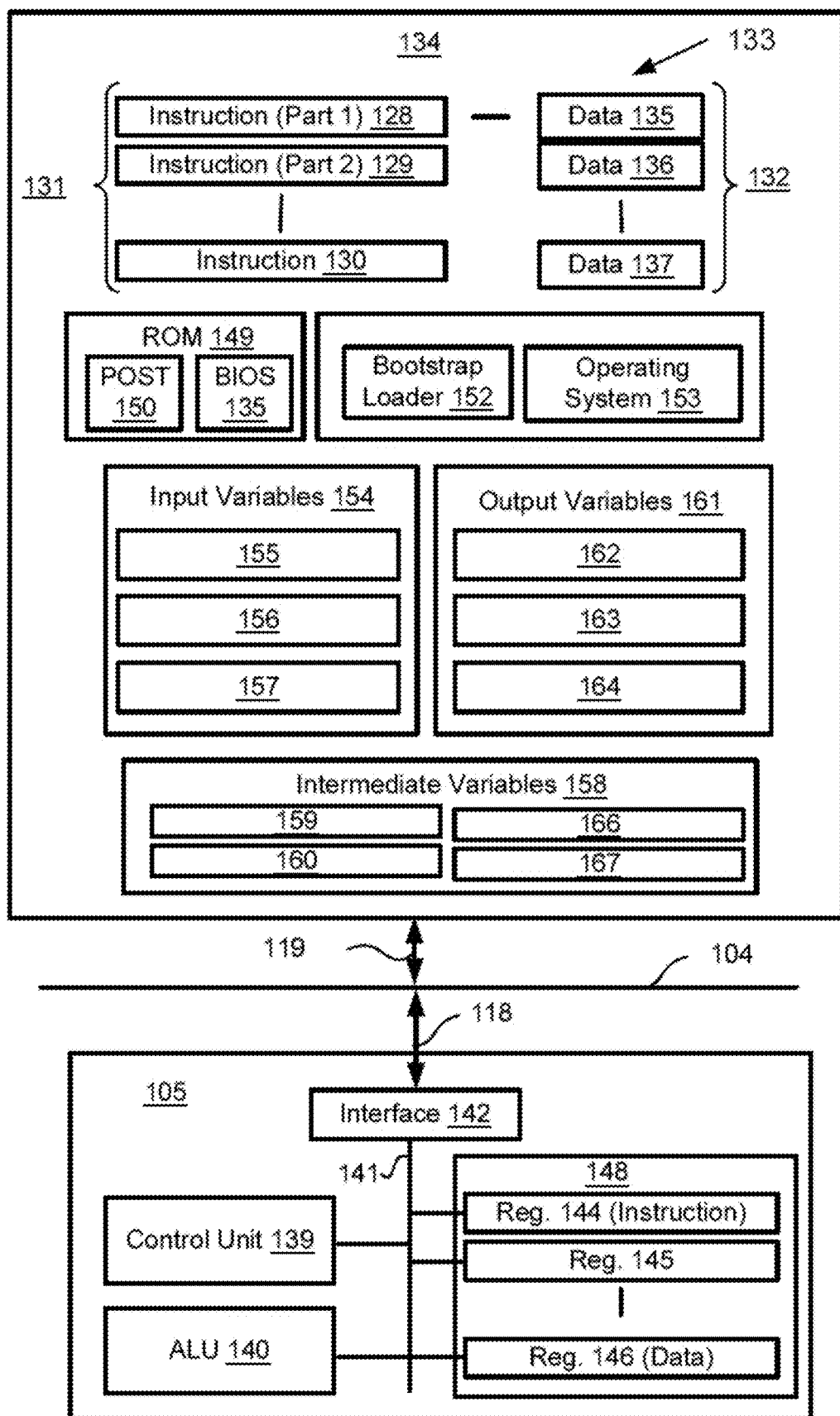

FIGS. 1A and 1B are block diagrams of a general-purpose computer system 100 upon which one can practice arrangements described in this specification. The following description is directed primarily to a computer server module 101. However, the description applies equally or equivalently to one or more remote terminals 168.

As seen in FIG. 1A, the computer system 100 includes: the server computer module 101; input devices such as a keyboard 102, a pointer device 103 (e.g., a mouse), a scanner 126, a camera 127, and a microphone 180; and output devices including a printer 115, a display device 114 and loudspeakers 117. An external Modulator-Demodulator (Modem) transceiver device 116 may be used by the computer server module 101 for communicating to and from the remote terminal 168 over a computer communications network 120 via a connection 121 and a connection 170. The aforementioned communication can take place between the remote terminal 168 and "the cloud" which in the present description comprises at least the one server module 101. The remote terminal 168 typically has input and output devices (not shown) which are similar to those described in regard to the server module 101. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer server module 101 typically includes at least one processor unit 105, and a memory unit 106. For example, the memory unit 106 may have semiconductor random access memory (RAM) and semiconductor read only memory (ROM). The remote terminal 168 typically includes as least one processor 169 and a memory 172. The computer server module 101 also includes a number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may include an Ethernet circuit card, a Bluetooth® wireless arrangement or an IEEE 802.11 wireless arrangement; however, numerous other types of interfaces may be practiced for the interface 111.

The I/O interfaces 108 and 113 may afford either or both of serial or parallel connectivity; the former may be implemented according to the Universal Serial Bus (USB) standards and having corresponding USB connectors (not illustrated). Storage memory devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119.

The techniques described in this specification may be implemented using the computer system 100, e.g., may be implemented as one or more software application programs 133 executable within the computer system 100. In some implementations, the one or more software application programs 133 execute on the computer server module 101 (the remote terminal 168 may also perform processing jointly with the computer server module 101), and a browser 171 executes on the processor 169 in the remote terminal, thereby enabling a user of the remote terminal 168 to access the software application programs 133 executing on the server 101 (which is often referred to as "the cloud") using the browser 171. In particular, the techniques described in this specification may be effected by instructions 131 (see FIG. 1B) in the software 133 that are carried out within the computer system 100. The software instructions 131 may be formed as one or more code modules, each for performing one or more particular tasks. The software may also be divided into two separate parts, in which a first part and the corresponding code modules performs the described techniques and a second part and the corresponding code modules manage a user interface between the first part and the user.

The software may be stored in a computer readable medium, including the storage devices described below, for example. The software is loaded into the computer system 100 from the computer readable medium, and then executed by the computer system 100. A computer readable medium having such software or computer program recorded on the computer readable medium is a computer program product. Software modules for that execute techniques described in this specification may also be distributed using a Web browser.

The software 133 is typically stored in the HDD 110 or the memory 106 (and possibly at least to some extent in the memory 172 of the remote terminal 168). The software is loaded into the computer system 100 from a computer readable medium, and executed by the computer system 100. Thus, for example, the software 133, which can include one or more programs, may be stored on an optically readable disk storage medium (e.g., CD-ROM) 125 that is read by the optical disk drive 112. A computer readable medium having such software or computer program recorded on it is a computer program product.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. For example, through manipulation of the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 can execute. The POST program 150 can be stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 can activate the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high-level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source 173, e.g., a brain imaging device 173 such as an MRI or DTI scanner, across one of the networks 120, 122, data retrieved from one of the storage devices 106, 109 or data retrieved from a storage medium 125 inserted into the corresponding reader 112, all depicted in FIG. 1A. The execution of a set of the instructions may in some cases result in output of data. Execution may also involve storing data or variables to the memory 134.

Some techniques described in this specification use input variables 154, e.g., data sets characterizing the brain of a patient, which are stored in the memory 134 in corresponding memory locations 155, 156, 157. The techniques can produce output variables 161, which are stored in the memory 134 in corresponding memory locations 162, 163, 164. Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle can include i) a fetch operation, which fetches or reads an instruction 131 from a memory location 128, 129, 130; ii) a decode operation in which the control unit 139 determines which instruction has been fetched; and iii) an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the techniques described in this specification may be associated with one or more segments of the program 133 and is performed by the register section 144, 145, 146, the ALU 140, and the control unit 139 in the processor 105 working together to perform the fetch, decode, and execute cycles for every instruction in the instruction set for the noted segments of the program 133. Although a cloud-based platform has been described for practicing the techniques described in this specification, other platform configurations can also be used. Furthermore, other hardware/software configurations and distributions can also be used for practicing the techniques described in this specification.

Figure 2A:
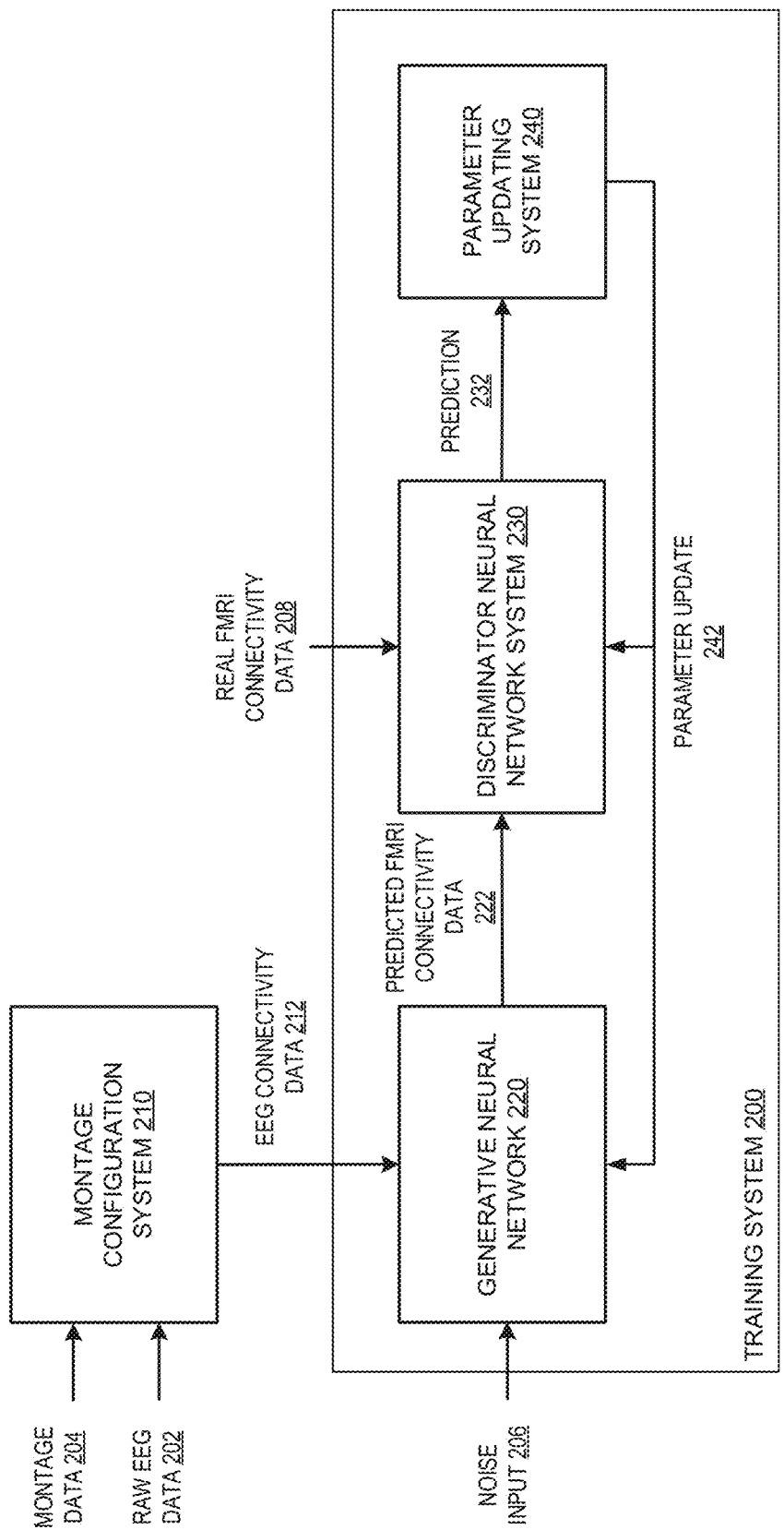
FIGS. 2A and 2B are diagrams of example training systems for training a generative neural network to generate predicted fMRI data.
Figure 2B:
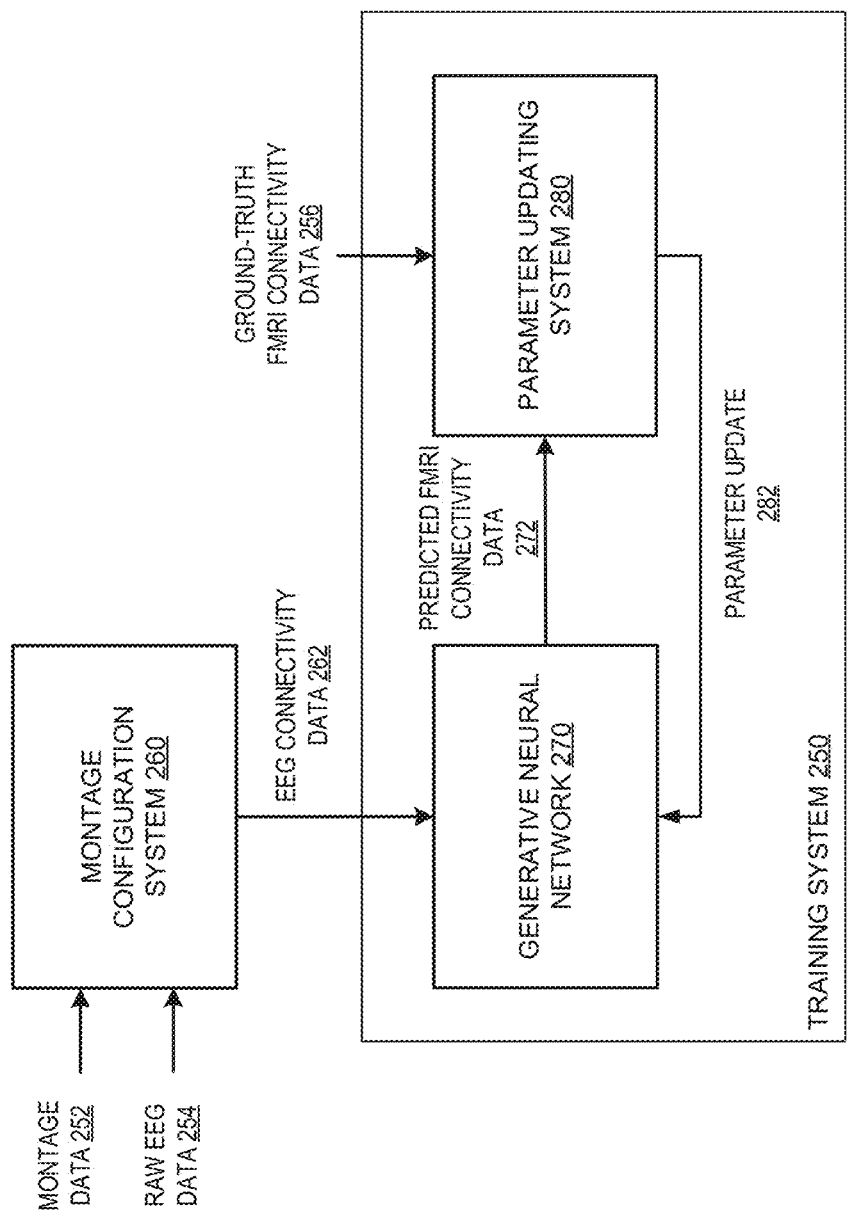

FIGS. 2A and 2B are diagrams of example training systems. FIG. 2A depicts a training system 200 that trains a generative neural network 220 to generate predicted fMRI data using adversarial learning. FIG. 2B depicts a training system 250 that trains a generative neural network 270 to generate predicted fMRI data using supervised learning.

Referring to FIG. 2A, the training system 200 includes the generative neural network 220, a discriminator neural network system 230, and a parameter updating system 240. The training system 200 is configured to receive EEG connectivity data 212 and use the EEG connectivity data 212 to train the generative neural network 220 to process the EEG connectivity data 212 to generate predicted fMRI connectivity data 222 corresponding to the EEG connectivity data 212.

The EEG connectivity data 212 includes, for each pair of parcellations in a first set of parcellations in the brain of a patient, a correlation between the brain activity of the pair of parcellations according to EEG data captured from the brain of the patient.

In some implementations, the EEG connectivity data 212 is generated from EEG data collected during multiple different sessions. That is, typically raw EEG data collected during a particular session includes a time series for each electrode of the EEG sensors; in some implementations, the EEG connectivity data 212 can be generated from EEG data that includes, for each electrode of the EEG sensor, multiple time series corresponding to respective sessions. In particular, for each of the multiple sessions, the EEG connectivity data 212 can include a correlation between each pair of parcellations in the first set of parcellations.

In some implementations, the EEG connectivity data 212 can include multiple channels corresponding to respective frequency bands of the EEG data. Frequency bands are discussed in more detail below.

The predicted fMRI connectivity data 222 includes, for each pair of parcellations in a second set of parcellations in the brain of the patient, a correlation between the brain activity of the pair of parcellations.

In some implementations, the first set of parcellations and the second set of parcellations are different. For example, the first set of parcellations can be a subset of the second set of parcellations. As a particular example, the second set of parcellations can include every parcellation in the brain of the patient, and the first set of parcellations can include each parcellation in the brain of the patient that is proximate to the surface of the brain of the patient, e.g., within a predetermined distance of the surface of the brain of the patient. Examples of EEG and fMRI connectivity data are described in more detail below with respect to FIG. 4.

The parcellations in the brain of the patient can be defined by a brain atlas. In this specification, a brain atlas is data that defines one or more parcellations of a brain of a patient, e.g., by defining in a common three-dimensional coordinate system the coordinates of the outline of the parcellation or the volume of the parcellation In some implementations, the training system 200 can receive the EEG connectivity data 212 from a montage configuration system 210. The montage configuration system 210 is configured to receive raw EEG data 202 captured using an EEG sensor and to generate the EEG connectivity data 212. The raw EEG data 202 can have multiple channels each corresponding to a respective electrode of the EEG sensor.

In some implementations, the montage configuration system 210 also receives as input montage data 204 characterizing a montage of the EEG sensor used to capture the raw EEG data 202. The montage data 204 can be any data characterizing the montage of the EEG sensor. For example, for each of multiple electrodes of the EEG sensor, the montage data 204 can identify a location on the scalp of the patient that the electrode is placed, e.g., by identifying a position in a common three-dimensional coordinate system of the EEG sensor.

In some such implementations, the montage data 204 depends on the patient. For example, the EEG sensor can have an initial montage that is common to all patients. The initial montage can be changed according to the particular shape of the head of the patient; that is, the location on the scalp of the patient of one or more electrodes of the EEG sensor can change from patient to patient.

Using the montage data 204, the montage configuration system 210 can perform source localization on the raw EEG data 202. That is, for each parcellation in the first set of parcellations, the montage configuration system 210 can determine a corresponding electrode of the EEG sensor. Typically the number of parcellations in the first set of parcellations is larger than the number of electrodes of the EEG sensor, so each electrode can have one or more corresponding parcellations. A parcellation corresponds to an EEG electrode if the raw EEG data 202 generated by the EEG electrode characterizes the brain activity of the parcellation.

For example, for each parcellation in the first set of parcellations, the montage configuration system 210 can determine the closest electrode of the EEG sensor on the scalp of the patient, and assign the parcellation to the determined closest electrode. As a particular example, the atlas can identify, for each parcellation, a location in the common three-dimensional coordinate system, and the montage configuration system 210 can determine a distance between each electrode and the parcellation in the common three-dimensional coordinate system in order to determine the closest electrode.

In some other implementations, the montage configuration system 210 does not have access to montage data 204 characterizing the montage of the EEG sensor used to capture the raw EEG data 202. In these implementations, the montage configuration system 210 can predict one or more parcellations that correspond to each channel of the raw EEG data 202, and then generate EEG connectivity data 212 according to the predicted mapping of EEG channels to parcellations.

For example, for each channel of the raw EEG data 202 (corresponding to a respective electrode of the EEG sensor), the montage configuration system 210 can process the channel of the raw EEG data 202 using a classification machine learning model to predict a particular parcellation in the first set of parcellations that corresponds to the channel. That is, the brain activity of the particular parcellation is represented by the channel of the raw EEG data 202 (e.g., the particular parcellation is the closest parcellation to the electrode corresponding to the channel of the raw EEG data 202). The classification machine learning model can be configured through training to process a channel of raw EEG data and to select a particular parcellation from a set of parcellations that corresponds to the channel of raw EEG data.

As a particular example, the classification machine learning model can be a recurrent neural network, e.g., a long short-term memory (LSTM) neural network or a gated recurrent unit (GRU) neural network, that is configured to process each element of the time series corresponding to the channel of raw EEG data 202 recurrently at respective processing time steps. At each processing time step, the recurrent neural network can process (i) the next element in the time series data and (ii) a hidden state of the recurrent neural network in order to update the hidden state of the recurrent neural network. In one or more of the processing time steps (in some implementations, at each processing time step), the recurrent neural network can also generate a network output corresponding to the current element in the time series data. The recurrent neural network can then process the one or more network outputs generated at respective processing time steps to generate the prediction for the particular parcellation corresponding to the channel of raw EEG data 202. For example, the recurrent neural network can process the final network output (i.e., the network output generated at the final processing time step) using one or more feedforward neural network layers and/or a softmax layer to generate the prediction. As another example, the recurrent neural network can combine the one or more network outputs (e.g., by determining the average of the network outputs), and process the combined network output (e.g., using one or more feedforward neural network layers and/or a softmax layer) to generate the prediction.

A training system can train the recurrent neural network using training examples that include i) training inputs that include multiple channels of raw EEG data corresponding to respective electrodes of the EEG sensor that captured the raw EEG data and ii) a ground-truth identification, for each channel of the raw EEG data, of the parcellation corresponding to the channel. For example, the ground-truth identifications can be determined according to montage data corresponding to the raw EEG data of the training example, as described above. For each training input, the training system can process the training input using the recurrent neural network to generate a predicted parcellation for each channel of the raw EEG data of the training input, and then determine an update to the parameters of the recurrent neural network according to an error between i) the predicted parcellations and ii) the respective ground-truth parcellations. The training system can use an appropriate classification loss function, e.g., categorical cross entropy loss or KL divergence.

After determining a predicted parcellation in the first set of parcellations for each channel of the raw EEG data 202 using the classification machine learning model, the montage configuration system 210 can assign, for each first parcellation in the first set of parcellations that was not one of the predicted parcellations, the first parcellation to a respective channel of the raw EEG data 202. That is, in some implementations, the EEG connectivity data 212 needs to have the same dimensionality for each set of raw EEG data 202, regardless of the number of electrodes on the EEG sensor used to capture the raw EEG data 202. Therefore, the EEG connectivity data 212 need to include elements corresponding to each parcellation in the first set of parcellations, even if the EEG sensor used to collect the raw EEG data 202 has relatively few electrodes, and thus some of the parcellations in the first set of parcellations were not assigned to a respective channel of the raw EEG data 202 using the classification machine learning model. For example, for each first parcellation in the first set of parcellations that was not one of the predicted parcellations determined by the classification machine learning model, the montage configuration system 210 can determine the closest parcellation that was one of the predicted parcellations determined by the classification machine learning model, and assign the first parcellation to the corresponding channel of the raw EEG data 202. For example, the montage configuration system 210 can determine the closest parcellation according to a brain atlas.

After determining an EEG electrode corresponding to each parcellation in the first set of parcellations (e.g., either using the montage data 204 or using a classification machine learning model as described above), the montage configuration system 210 can generate the EEG connectivity data 212. For each pair of parcellations in the first set of parcellations, the montage configuration system 210 can determine the correlation between the brain activity of the parcellations by determining the correlation between the raw EEG data 202 generated by the respective EEG electrodes corresponding to the pair of parcellations. The montage configuration system 210 can then provide the EEG connectivity data 212 to the training system 200.

The training system 200 provides the EEG connectivity data 212 to the generative neural network 220 to generate the predicted fMRI connectivity data 222. The generative neural network 220 can have any appropriate neural network architecture. For example, the generative neural network 220 can be a feedforward neural network. As another example, the generative neural network 220 can be a recurrent neural network, e.g., an LSTM neural network or a GRU neural network, that is configured to recurrently process each element or groups of elements of the EEG connectivity data 212 (e.g., each column or row of an EEG connectivity matrix represented by the EEG connectivity data 212) recurrently at respective processing time steps to generate corresponding elements or groups of elements of the predicted fMRI connectivity data 222.

In some implementations, the generative neural network 220 can also receive as input a noise input 206. For example, the noise input 206 can be randomly sampled from a predetermined distribution, e.g., a normal distribution.

After the generative neural network 220 generates the predicted fMRI connectivity data 222, the training system 200 can provide the predicted fMRI connectivity data 222 to the discriminator neural network system 230. The training system 200 can train the discriminator neural network system 230 to process a predicted fMRI connectivity data 222 and to generate a prediction 232 of whether the fMRI connectivity data is real, i.e., generated from fMRI data that has been captured from the brain of the patient, or synthetic, i.e., generated by the generative neural network 220.

The discriminator neural network system 230 can have any appropriate neural network architecture. For example, the discriminator neural network system 230 can include a discriminator neural network that has the same or a similar neural network architecture as the generative neural network 220. That is, if the generative neural network 220 is a feedforward neural network, then the discriminator neural network can also be a feedforward neural network (e.g., followed by a classification layer that generates the prediction 232 of whether the fMRI connectivity data is real or synthetic). Similarly, if the generative neural network 220 is a recurrent neural network, then the discriminator neural network can also be a recurrent neural network (e.g., followed by a classification layer).

In some implementations, the discriminator neural network system 230 can include one or more discriminator neural networks that each process the predicted fMRI connectivity data 222 and predict whether the predicted fMRI connectivity data 222 is real or synthetic.

The discriminator neural network system 230 can combine the respective predictions of the one or more discriminator neural networks to generate the prediction 232. For example, the discriminator neural network system 230 can determine a mean or sum of the respective predictions. As another example, the discriminator neural network system 230 can combine the respective prediction using a voting algorithm.

The parameter updating system 240 can obtain the prediction 232 generated by the discriminator neural network system 230 and determine a parameter update 242 according to an error in the prediction 232. Examples of the error (as computed according to a particular loss function) are provided below. The training system 200 can apply the parameter update 242 to the parameters of the generative neural network 220 and the discriminator neural network system 230. That is, the training system 200 can train the generative neural network 220 and the discriminator neural networks in the discriminator neural network system 230 concurrently.

Generally, the parameter updating system 240 determines the parameter update 242 to the parameters of the generative neural network 220 in order to increase the error in the prediction 232. For example, if the discriminator neural network system 230 correctly predicted that the predicted fMRI connectivity data 222 is synthetic, then the parameter updating system 240 generates a parameter update 242 to the parameters of the generative neural network 220 in order to improve the realism of the predicted fMRI connectivity data 222 so that the discriminator neural network system 230 might incorrectly predict the next predicted fMRI connectivity data 222 to be real.

Conversely, the parameter updating system 240 determines the parameter update 242 to the parameters of the discriminator neural network system 230 in order to decrease the error in the prediction 232. For example, if the discriminator neural network system 230 incorrectly predicted that the predicted fMRI connectivity data 222 is real, then the parameter updating system 240 generates a parameter update 242 to the parameters of the discriminator neural network system 230 in order to improve the predictions 232 of the discriminator neural network system 230.

In some implementations in which the discriminator neural network system 230 includes multiple different discriminator neural networks, the parameter updating system 240 determines a parameter update 242 for each discriminator neural network using the prediction 232 output by the discriminator neural network system 230. That is, the parameter updating system 240 determines a parameter update 242 for each particular discriminator neural network using the same combined prediction 232 that was generated by combining the respective predictions of the multiple discriminator neural networks, regardless of the respective prediction generated by the particular discriminator neural network.

In some other implementations in which the discriminator neural network system 230 includes multiple different discriminator neural networks, the parameter updating system 240 determines a parameter update 242 for each discriminator neural network using the respective prediction generated by the discriminator neural network. That is, the parameter updating system 240 generates the parameter update 242 for a particular discriminator in order to improve the respective prediction generated by the particular discriminator (which will indirectly improve the combined prediction 232 output by the discriminator neural network system 230 because the combined prediction 232 is generated according to the respective predictions generated by the multiple discriminator neural networks).

During training, the training system 200 can also provide real fMRI connectivity data 208 to the discriminator neural network system 230. Each discriminator neural network in the discriminator neural network system 230 can process the real fMRI connectivity data 208 to predict whether the real fMRI connectivity data 208 is a real or synthetic example of fMRI connectivity data. Again, the discriminator neural network system 230 can combine the respective predictions of each of the discriminator neural networks to generate a second prediction 232. The parameter updating system 240 can then determine a second parameter update 242 to the parameters of discriminator neural network system 230 according to an error in the second prediction 232. Generally, the training system 200 does not use the second prediction corresponding to the real fMRI connectivity data 208 to update the parameters of the generative neural network 220.

As a particular example, parameter updating system 240 can use the Wasserstein loss function to determine the parameter update 242, which is:

$$D(x)-D(G(z)),$$

where $D(x)$ is the likelihood assigned by the discriminator neural network system 230 that a real fMRI connectivity data 208 is real, $G(z)$ is synthetic fMRI connectivity data 222 generated by the generative neural network 220, and $D(G(z))$ is the likelihood assigned by the discriminator neural network system 230 that the synthetic fMRI connectivity data 222 is real. The objective of the generative neural network 220 is to minimize Wasserstein loss by maximizing $D(G(z))$, i.e. by causing the discriminator neural network system 230 to predict that synthetic fMRI connectivity data 222 is real. The objective of the discriminator neural network system 230 is to maximize Wasserstein loss, i.e. correctly predict both real and synthetic fMRI connectivity data.

As another particular example, the parameters updating system 240 can use the following loss function:

$$\log(D(x))+\log(1-D(G(z)))$$

where again the objective of the generative neural network 220 is to minimize the loss and the objective of the discriminator neural network system 230 is to maximize the loss.

The training system 200 can backpropagate the loss through both the generative neural network 220 and the discriminator neural network system 230, thus training both networks concurrently.

In some implementations, after the training system 200 has completed training of the generative neural network 220 (i.e., after the training system 200 has generated final parameter values for the generative neural network 220), the generative neural network 220 and, optionally, the montage configuration system 210 can be deployed on an inference system that is configured to generate predicted fMRI connectivity data. That is, at inference time, the inference system can process EEG connectivity data 212 or raw EEG data 202 to generate predicted fMRI connectivity data 222. Typically, the inference system does not include the discriminator neural network system 230 or the parameter updating system 240.

In some such implementations, at inference time, the inference system can receive raw EEG data 202 that has been captured using an EEG sensor that has a particular montage that was not seen during training. Even if the montage configuration system 210 has never received raw EEG data 202 corresponding to the particular montage before, the montage configuration system 210 can generate EEG connectivity data 212 that can be processed by the generative neural network 220 to generate predicted fMRI connectivity data 222. For example, the first set of parcellations can be the same regardless of the montage data 204, and so the montage configuration system 210 can generate EEG connectivity data 212 that has the same shape and size (and can therefore be received by the generative neural network 220) regardless of the montage corresponding to the raw EEG data 202.

After generating the predicted fMRI connectivity data 222, the inference system can provide the predicted fMRI connectivity data 222 to an external system for further processing, e.g., a graphical user interface and/or a machine learning system.

The graphical user interface can display data characterizing the predicted fMRI connectivity data 222 to a user. For example, the graphical user interface 250 can display a connectivity matrix characterizing the predicted fMRI connectivity data 222. Example connectivity matrices are discussed below with respect to FIG. 4.

The machine learning system can include one or more machine learning models that are configured to process the predicted fMRI connectivity data 222 and generate a model output that is clinically relevant for a user. For example, a machine learning model can process the predicted fMRI connectivity data 222 to generate a prediction for whether the patient has a particular brain disease, e.g., autism, depression, or schizophrenia.

In some other implementations, after the training system 200 has completed training of the generative neural network 220, the generative neural network 220 and/or the discriminator neural network system 230 can be deployed on an anomaly detection system that is configured to predict whether brain data of a patient is anomalous. In this specification, a set of brain data is "anomalous" if the values of the brain data are outside a normal range of values.

For example, the anomaly detection system can process input EEG data (e.g., raw EEG data 202 or EEG connectivity data 212) and predict whether the input EEG data is anomalous. In particular, the anomaly detection system can process the input EEG data using the generative neural network 220 (and, optionally, the montage configuration system 210 as described above) to generate predicted fMRI connectivity data 222. The anomaly detection system can then process the predicted fMRI connectivity data 222 using the discriminator neural network system 230 to predict whether the predicted fMRI connectivity data 222 is real or synthetic, as described above. If the discriminator neural network system 230 predicts that the predicted fMRI connectivity data 222 is synthetic, then the anomaly detection system can determine that the input EEG data may be anomalous. For example, if the discriminator neural network system 230 is configured to generate a prediction 232 that is a scalar value between 0 and 1 that represents a likelihood that the predicted fMRI connectivity data 222 is synthetic (i.e., where 1 represents high confidence that the fMRI connectivity data 222 is synthetic and 0 represents high confidence that the fMRI connectivity data 222 is real), then the anomaly detection system can determine the input EEG data to be anomalous if the prediction 232 generated by the discriminator neural network system 230 exceeds a predetermined threshold, e.g., 0.5, 0.9, or 0.95.

Because the generative neural network 220 has been configured through training by the training system 200 to generate predicted fMRI data 222 that is realistic, generally if the input EEG data is within a normal range, then the generative neural network 220 will generate predicted fMRI connectivity data 222 that is predicted to be real by the discriminator neural network system 230. However, if the input EEG data is not within a normal range, i.e., if the input EEG data is anomalous, then the generative neural network 220 may generate predicted fMRI connectivity data 222 that is also outside of a normal range of fMRI connectivity data. Because the discriminator neural network system 230 is configured to identify fMRI connectivity data that does not seem realistic (i.e., that is outside of the normal range of fMRI connectivity data), the discriminator neural network system 230 will predict that the predicted fMRI connectivity data 222 is synthetic (i.e., anomalous).

As another example, the anomaly detection system can process input fMRI data (e.g., real fMRI connectivity data 208) and predict whether the fMRI data is anomalous. In particular, the anomaly detection system can process fMRI data using and the discriminator neural network system to predict whether the fMRI data is real or synthetic, as described above. If the discriminator neural network system 230 predicts that the fMRI data is synthetic, then the anomaly detection system can determine that the fMRI data may be anomalous. For example, if the discriminator neural network system 230 is configured to generate a prediction 232 that is a scalar value between 0 and 1 that represents a likelihood that the fMRI data is synthetic (i.e., where 1 represents high confidence that the fMRI data is synthetic and 0 represents high confidence that the fMRI data is real), then the anomaly detection system can determine the fMRI data to be anomalous if the prediction 232 generated by the discriminator neural network system 230 exceeds a predetermined threshold, e.g., 0.5, 0.9, or 0.95. In other words, in these implementations, only the trained discriminator neural network system 230 can be deployed on the anomaly detection system, and can process real fMRI data 208 to determine whether the real fMRI data 208 is anomalous.

Because the discriminator neural network system 230 has been configured through training using both real and synthetic fMRI data to determine whether the fMRI data is realistic, generally if the input fMRI data is within a normal range, then the discriminator neural network system 230 will predict the input fMRI data to be real. However, if the input fMRI data is not within a normal range, i.e., if the input fMRI data is anomalous, then the discriminator neural network system 230 may predict that the fMRI data is synthetic (i.e., anomalous).

Referring to FIG. 2B, the training system 250 includes the generative neural network 270 and a parameter updating system 280. The training system 200 is configured to receive EEG connectivity data 262 and use the EEG connectivity data 262 to train the generative neural network 270 to process the EEG connectivity data 262 to generate predicted fMRI connectivity data 272 corresponding to the EEG connectivity data 262.

As described above, the EEG connectivity data 262 includes, for each pair of parcellations in a first set of parcellations in the brain of a patient, a correlation between the brain activity of the pair of parcellations according to EEG data captured from the brain of the patient. In some implementations, the EEG connectivity data 212 includes EEG data collected at multiple different sessions. In some implementations, the EEG connectivity data 212 includes multiple channels corresponding to respective frequency bands of the EEG data. The predicted fMRI connectivity data 272 includes, for each pair of parcellations in a second set of parcellations in the brain of the patient, a correlation between the brain activity of the pair of parcellations.

As described above, in some implementations, the training system 250 can receive the EEG connectivity data 262 from a montage configuration system 260. The montage configuration system 260 is configured to receive raw EEG data 252 captured using an EEG sensor and to generate the EEG connectivity data 262. For example, the montage configuration system 260 can generate the EEG connectivity data 262 using montage data 254 that characterizes the montage of the EEG sensor. As another example, the montage configuration system 260 can generate the EEG connectivity data 262 using a classification machine learning model that is configured to predict, for each channel of the raw EEG data 252, a corresponding parcellation in the brain of the patient, as described above.

The generative neural network 270 can have any appropriate neural network architecture. For example, the generative neural network 270 can have a neural network architecture described above with respect to the generative neural network 220 depicted in FIG. 2A.

After the generative neural network 270 generates the predicted fMRI connectivity data 272, the training system 250 can provide the predicted fMRI connectivity data 272 to the parameter updating system 280, which is configured to determine a parameter update 282 to the parameters of the generative neural network 270 according to an error in the predicted fMRI connectivity data 272.

To determine the error in the predicted fMRI connectivity data 272, the parameter updating system 280 can obtain ground-truth fMRI connectivity data 256 corresponding to the patient. That is, the ground-truth fMRI connectivity data 256 has been generated from fMRI data that was collected from the brain of the patient. Therefore, the ground-truth fMRI connectivity data 256 represents what the generative neural network 270 should have generated in response to processing the EEG connectivity data 262.

In some implementations, the fMRI data used to generate the ground-truth fMRI connectivity data 256 was captured from the brain of the patient at the same time that the raw EEG data 254 was captured.

In some other implementations, the fMRI data used to generate the ground-truth fMRI connectivity data 256 was captured from the brain of the patient at a different time than the time at which the raw EEG data 254 was captured. Doing this can be preferable to capturing the raw EEG data 254 and the fMRI data concurrently, because the goal of the generative neural network 270 is to generate predicted fMRI connectivity data 272 that represents the default state of the brain of the patient, rather than the state of the patient at the time that the raw EEG data 254 was captured. Data representing the default state of the brain of the patient can encode information that is useful, e.g., when determining whether the patient has a brain disease. In particular, the fMRI data and raw EEG data 254 can be resting state data; i.e., the fMRI data and raw EEG data 254 can be captured when the patient is not performing a task.

The parameter updating system 280 can determine an error between i) the predicted fMRI connectivity data 272 and ii) the ground-truth fMRI connectivity data 256, and generate the parameter update 282 according to the determined error. For example, the parameter updating system 280 can update the parameters of the generative neural network 270 using gradient descent and backpropagation.

Figure 2C:
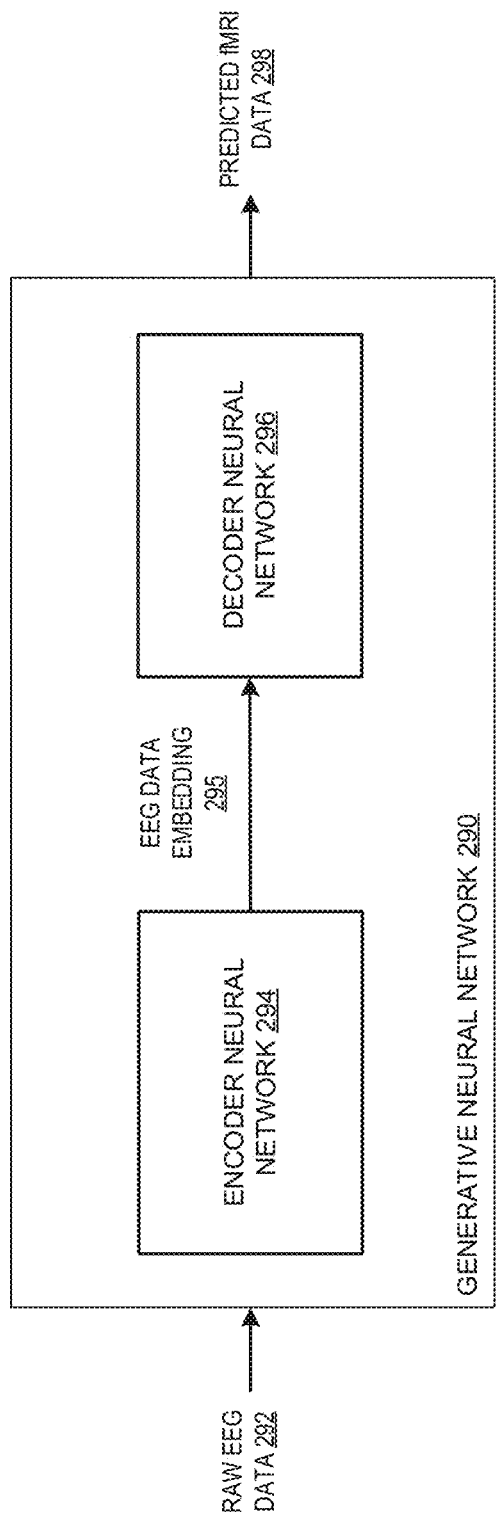
FIG. 2C is a diagram of an example generative neural network configured to generate predicted fMRI data.

FIG. 2C is a diagram of an example generative neural network 290 that has been configured through training to generate predicted fMRI data 298. In particular, the generative neural network 290 is configured to obtain raw EEG data 292 and to process the raw EEG data 292 to generate the predicted fMRI data 298 corresponding to the raw EEG data 292.

The raw EEG data 292 includes multiple channels each corresponding to a respective electrode of the EEG sensor used to capture the raw EEG data 292. Each channel of the raw EEG data 292 is a time series of elements representing brain activity recorded by the corresponding electrode of the EEG sensor at respective time points.

The predicted fMRI data 298 generated by the generative neural network 290 in response to processing the raw EEG data 292 includes multiple channels each corresponding to a respective parcellation in the brain of the patient. For example, the predicted fMRI data 298 can have the same number of channels as the raw EEG data 292. Each channel of the predicted fMRI data 298 is a time series of elements representing brain activity of a particular parcellation in the brain of the patient at respective time points. For example, if the predicted fMRI data 298 has the same number of channels as the raw EEG data 292, then each channel of the predicted fMRI data 298 can represent the brain activity of the parcellation closest to the EEG electrode used to capture the corresponding channel of the raw EEG data 292. In some implementations, the number of time points represented in the predicted fMRI data 298 is the same as the number of time points represented in the raw EEG data 292.

In some implementations, the generative neural network 290 determines, for each channel of the raw EEG data 292, a corresponding parcellation in the brain of the patient, e.g., the parcellation closest to the EEG electrode used to capture the channel of the raw EEG data 292. For example, as described above with respect to FIG. 2A, the generative neural network 290 can determine the parcellation corresponding to each channel using montage data characterizing the montage of the EEG sensor used to capture the raw EEG data 292, or by processing the raw EEG data 292 using a classification machine learning model. The generative neural network can then use the identifications of the respective parcellations when processing the raw EEG data 292 to generate the predicted fMRI data 298. For example, when processing a respective channel of the raw EEG data 292, the generative neural network can also process an embedding of the identification of the corresponding parcellation, e.g., a one-hot encoding of the corresponding parcellation.

In some implementations, the generative neural network 290 includes an encoder neural network 294 and a decoder neural network 296. The encoder neural network 294 can be configured through training to process the raw EEG data 292 and to generate an embedding 295 of the raw EEG data 292. In this specification, an embedding is an ordered collection of numeric values that represents an input in a particular embedding space. For example, an embedding can be a vector of floating point or other numeric values that has a fixed dimensionality.

For example, the encoder neural network 294 can process each channel of the raw EEG data 292 using a recurrent neural network, e.g., an LSTM neural network or a GRU neural network, to generate the embedding 295. In some implementations, the embedding 295 of the raw EEG data 292 has the same number of channels as the raw EEG data 292. In some other implementations, the embedding 295 is a single high-dimensional tensor.

The decoder neural network 296 can be configured through training to process the embedding 295 of the raw EEG data 292 and to generate the predicted fMRI data 298. For example, in implementations in which the embedding 295 of the raw EEG data 292 include multiple channels (e.g., a respective channel corresponding to each channel of the raw EEG data 292), then the decoder neural network 296 can process each channel of the embedding 295 using a recurrent neural network, e.g., an LSTM neural network or a GRU neural network, to generate a respective channel of the predicted fMRI data 298.

In some implementations, a training system trains the generative neural network 290 in an adversarial fashion, as described above with respect to FIG. 2A. That is, a discriminator neural network system can be configured to process the predicted fMRI data 298 to predict whether the predicted fMRI data 298 is real or synthetic, and the training system can determine an update to the parameters of the generative neural network 290 according an error in the prediction of the discriminator neural network system. After training, the generative neural network 290 can be deployed on an inference system that is configured to process raw EEG data 292 to generate predicted fMRI data 298. Instead or in addition, the generative neural network 290 and the discriminator neural network system can be deployed on an anomaly detection system that is configured to predict whether raw EEG data 292 is anomalous, as described above with respect to FIG. 2A. That is, the anomaly detection system can process raw EEG data 292 using the generative neural network 290 to generate predicted fMRI data 298, and then process the predicted fMRI data 298 using the discriminator neural network system to generate a prediction of whether the predicted fMRI data 298 is real or synthetic. if the discriminator neural network system predicted that the predicted fMRI data 298 is synthetic, then the anomaly detection system can determine that the raw EEG data 292 may be anomalous.

In some other implementations, a training system trains the generative neural network 290 in a supervised fashion, as described above with respect to FIG. 2B. That is, the training system can process raw EEG data 292 using the generative neural network 290 to generate predicted fMRI data 298, and then determine an error between i) the predicted fMRI data 298 and ii) ground-truth fMRI data corresponding to the raw EEG data 292. The ground-truth fMRI data has been generated from fMRI data that was collected from the brain of the same patient as the raw EEG data 292. As described above with respect to FIG. 2B, in some implementations, the ground-truth fMRI data was captured from the brain of the patient at the same time that the raw EEG data 292 was captured, while in some other implementations, the ground-truth fMRI data was captured from the brain of the patient at a different time than the time at which the raw EEG data 292 was captured. The training system can determine an update to the parameters of the generative neural network 290 according to the error, e.g., using backpropagation and stochastic gradient descent.

Figure 3:
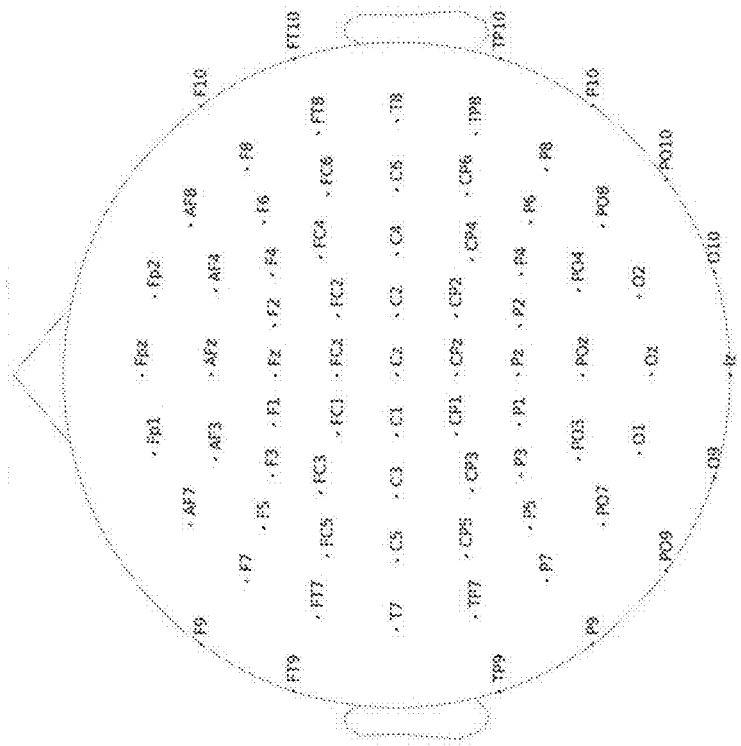
FIG. 3 illustrates example EEG montages.
Figure 3:
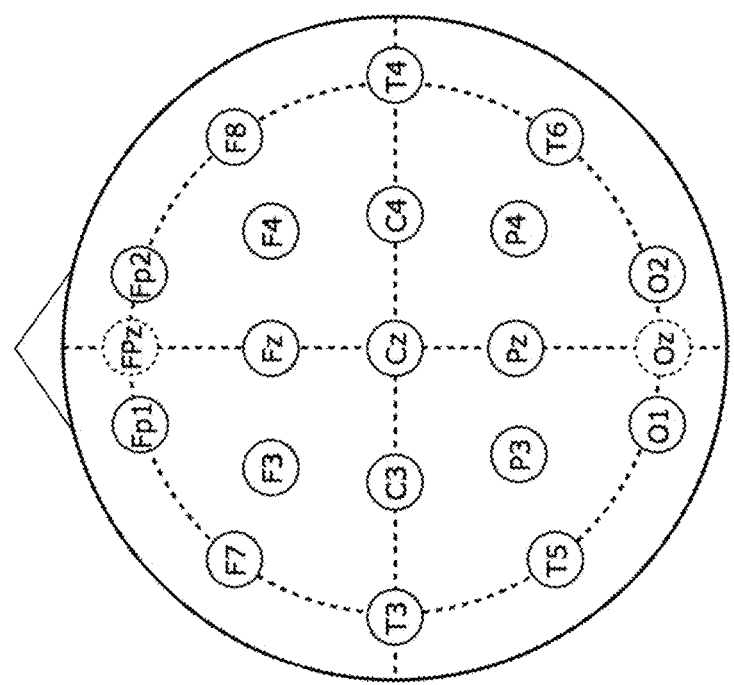

FIG. 3 illustrates example EEG montages 310 and 320. The montages 310 and 320 characterize the placement of electrodes of respective EEG sensors on the scalp of patients.

In particular, the first montage 310 corresponds to an EEG sensor that has 21 electrodes, while the second montage 320 corresponds to an EEG sensor that has 74 electrodes.

A generative neural network, e.g., the generative neural network 220 depicted in FIG. 2A, the generative neural network 270 depicted in FIG. 2B, or the generative neural network 290 depicted in FIG. 2C, can be configured through training to generate predicted fMRI data using EEG data captured by the EEG sensors corresponding to the montages 310 and 320. That is, regardless of the number of electrodes of an EEG sensor or the placement of the electrodes on the scalp of the patient, the generative neural network can generate predicted fMRI data using the EEG data captured by the EEG sensor.

A system, e.g., the training system 200 depicted in FIG. 2A or the training system 250 depicted in FIG. 2B, can determine a minimum number of electrodes required to generate accurate predicted fMRI data. For example, for each of multiple EEG sensors that have different numbers of electrodes, the system can process EEG data captured by the EEG sensor to generate predicted fMRI data. The system can then determine an accuracy of the generated predicted fMRI data, e.g., by determining an error between the predicted fMRI data and ground-truth fMRI data captured from the brain of the same patient as the EEG data.

The system can determine a relationship between the number of electrodes of an EEG sensor and the accuracy of predicted fMRI data generated from EEG data captured from the EEG sensor. As a particular example, the system can plot the accuracy of the predicted fMRI data corresponding each EEG sensor with respect to the respective number of electrodes of the EEG sensors. The system can then determine a minimum number of electrodes required to achieve a particular accuracy, and only accept EEG data as input to the generative neural network if the EEG data was captured by an EEG sensor that has at least the minimum number of electrodes.

Figure 4:
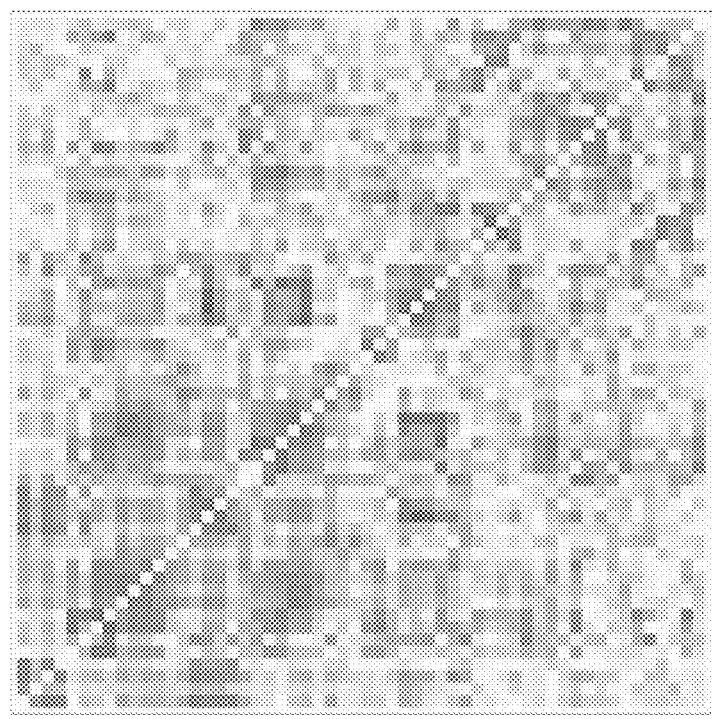
FIG. 4 illustrates example connectivity matrices.
Figure 4:
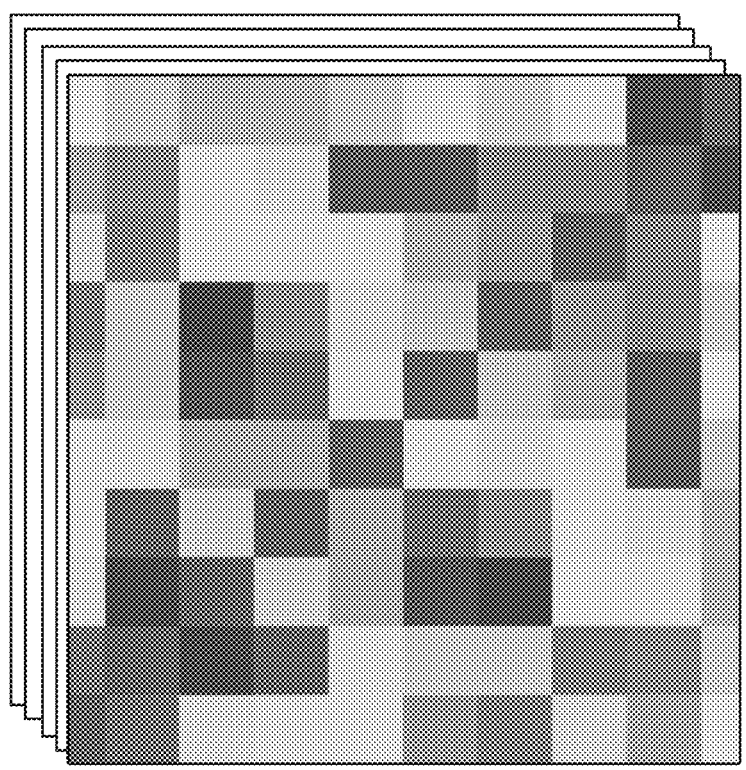

FIG. 4 illustrates example connectivity matrices 410 and 420. In particular, a set of EEG connectivity matrices 410 was generated using EEG data captured from the brain of a patient, and an fMRI connectivity matrix 420 was generated using fMRI data captured from the brain of the patient.

Each connectivity matrix characterizes, for each pair of parcellations in a set of parcellations, a correlation between the brain activity of the pair of parcellations. As depicted in FIG. 4, the EEG connectivity matrices 410 correspond to a first set of parcellations and the fMRI connectivity matric 420 corresponds to a second set of parcellations. Each row and column of the connectivity matrices 410 and 420 corresponds to a parcellation, and each element has a value identifying the correlation between the parcellation corresponding to the row of the element and the parcellation corresponding to the column of the element. In some implementations, the connectivity matrices 410 and 420 can include ranges of two different colors, where the first color corresponds to negative correlations and the second color corresponds to positive correlations, and the intensity of a color corresponds to a magnitude of the negative or positive correlation.

Each EEG connectivity matrix in the set of EEG connectivity matrices 410 corresponds to a different respective frequency band of the EEG data. To generate the EEG connectivity matrix 410 corresponding to a particular frequency band, a system, e.g., the montage configuration system 210 depicted in FIG. 2A or the montage configuration system 260 depicted in FIG. 2B, can determine, for each pair of parcellations in the first set of parcellations, the correlation between the brain activity within the particular frequency band of the pair of parcellations.

For example, the system can perform a Fourier decomposition of the EEG data into the multiple different frequency bands. As a particular example, the multiple different frequency bands can include the delta frequency band (typically 1-3 Hz), theta frequency band (typically 4-7 Hz), alpha frequency band (typically 8-12 Hz), beta frequency band (typically 13-25 Hz), and gamma frequency band (typically 30-45 Hz).

Different information can be encoded into the EEG connectivity matrices 410 corresponding to different frequency bands. For example, the theta frequency band can encode, for each pair of parcellations, information characterizing a signal between the pair of parcellations identifying the expectations of the parcellations, while the beta frequency band can encode, for each pair of parcellations, information characterizing a feedback signal.

As depicted in FIG. 4, the first set of parcellations (corresponding to the EEG connectivity matrices 410) is smaller than the second set of parcellations (corresponding to the fMRI connectivity matrix 420). For example, the first set of parcellation scan be a subset of the second set of parcellations.

A generative neural network, e.g., the generative neural network 220 depicted in FIG. 2A or the generative neural network 270 depicted in FIG. 2B, can be configured through training to generated a predicted fMRI connectivity matrix (characterizing a prediction of the fMRI connectivity matrix 420) using the EEG connectivity matrices 410. In particular, the generative neural network can predict the correlation between particular pairs of parcellations that are in the second set of parcellations but that are not in the first set of parcellations, even though the EEG connectivity matrices does not explicitly encode information about the particular pairs of parcellations. The generative neural network can do this because the respective brain activity of parcellations in the brain of the patient are not independent of each other.

As a particular example, the first set of parcellations can include parcellations proximate to the surface of the brain of the patient and the second set of parcellations can include every parcellation in the brain of the patient. That is, the fMRI connectivity matrix 420 (and the predicted fMRI connectivity matrix generated by the generative neural network) includes information about parcellations that are not proximate to the surface while the EEG connectivity matrices 410 do not. These parcellations can include parcellations from the hippocampus, amygdala, cingulate cortex, temporal lobe, and orbital frontal cortex of the brain of the patient, which are important regions of the brain for predicting brain disease. Therefore, the fMRI connectivity matrix can be more useful to clinicians than the EEG connectivity matrices 410 when working to determine whether a patient has a brain disease. The generative neural network can provide clinicians with a predicted fMRI connectivity matrix when fMRI data is not available, which can encode information that is helpful to a clinician or researcher.

Figure 5:
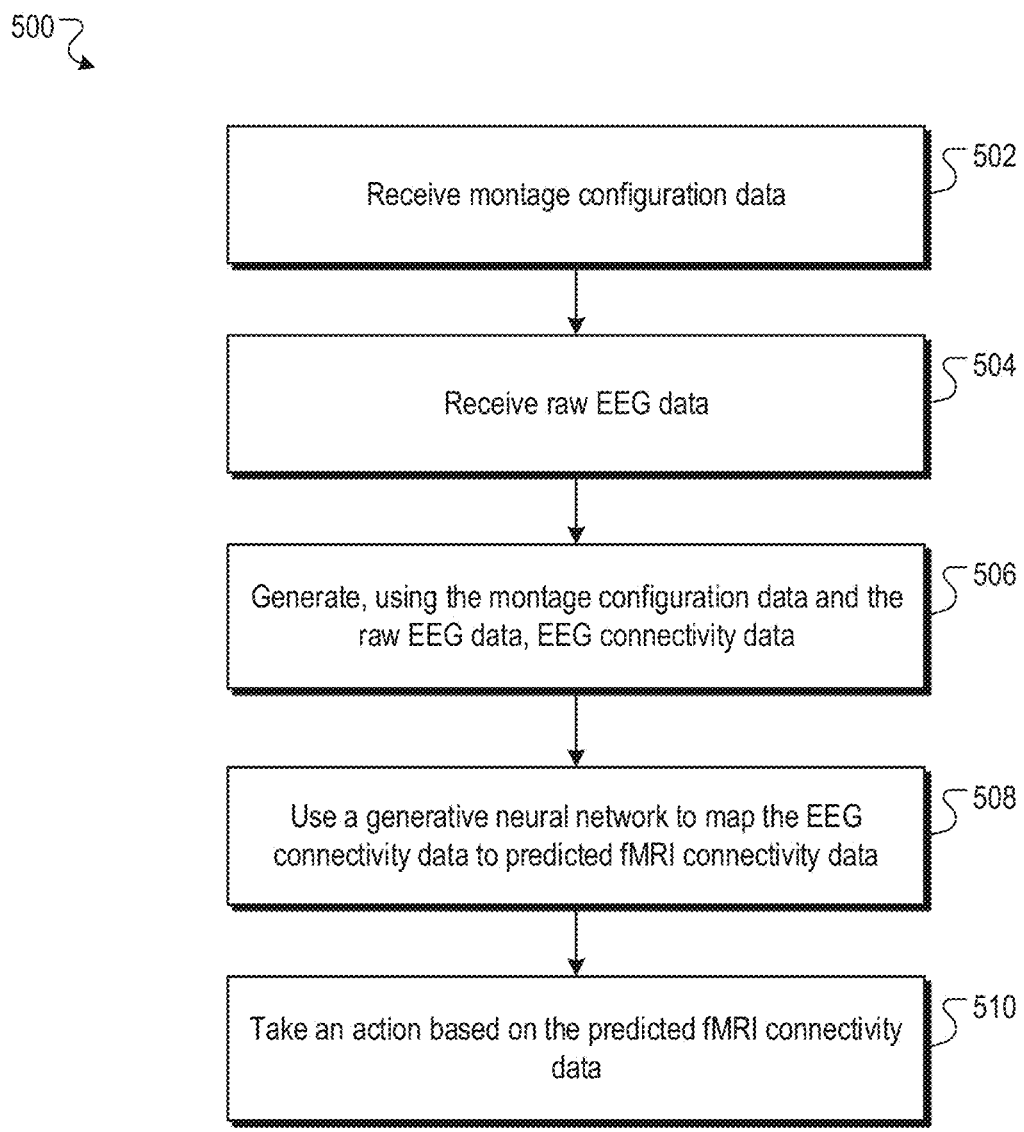
FIG. 5 is a flowchart of an example process for generating predicted brain data.

FIG. 5 is a flowchart of an example process 500 for generating predicted brain data. The process 500 can be implemented by one or more computer programs installed on one or more computers and programmed in accordance with this specification. For example, the process 500 can be performed by the computer server module depicted in FIG. 1A. For convenience, the process 500 will be described as being performed by a system of one or more computers.

The system receives montage configuration data for a specified montage (step 502).

The system receives raw EEG data that has been captured using the specified montage from the brain of a subject (step 504).

The system generates, using the montage configuration data and the raw EEG data, EEG connectivity data (step 506). The EEG connectivity data can represent, for each pair of parcellations in a first set of parcellations, a correlation between brain activity of the pair of parcellations. In some implementations, the first set of parcellations includes parcellations that are proximate to the surface of the brain of the subject, e.g., that are within a threshold distance of the surface.

The EEG connectivity data can include multiple channels corresponding to respective frequency bands of the raw EEG data. For example, the system can perform Fourier decomposition on the raw EEG data to generate the different channels of the EEG connectivity data.

Generating the EEG connectivity data can include performing source localization. For example, the system can determine, for each of multiple electrodes of the specified montage, one or more corresponding parcellations whose brain activity is captured by the electrode.

The system uses a generative neural network to map the EEG connectivity data to predicted fMRI connectivity data (step 508). In some implementations, the generative neural network has been trained using adversarial learning. For example, the generative neural network can be trained using a generative adversarial network (GAN), e.g., using the training system 200 depicted in FIG. 2A. The generative neural network can be trained using training EEG-fMRI connectivity data pairs that each include i) EEG connectivity data of a subject and ii) fMRI connectivity data of the same subject.

The predicted fMRI connectivity data can represent, for each pair of parcellations in a second set of parcellations, a correlation between brain activity of the pair of parcellations. In some implementations, the first set of parcellations is smaller than the second set of parcellations. For example, the first set of parcellations can be a subset of the second set of parcellations.

The system takes an action based on the predicted fMRI connectivity data (step 510). Taking the action can include one or more of: using the predicted fMRI connectivity data as input to one or more machine learning models; displaying the fMRI connectivity data to a user; categorizing the particular subject as having a particular brain condition; determining the particular subject as a candidate for neurosurgery; automatically determining that the particular subject should undergo further testing for a particular brain condition; or applying transcranial magnetic stimulation based at least in part on the predicted fMRI connectivity data.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g, a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

In addition to the embodiments described above, the following embodiments are also innovative:

Embodiment 1 is a method comprising:
receiving montage configuration data for a specified montage;
receiving raw EEG data captured using the specified montage from a brain of a particular subject;
generating, using the montage configuration data and the raw EEG data, EEG connectivity data for the specified montage;
using a generative neural network to map the EEG connectivity data to predicted fMRI connectivity data, the generative neural network having been trained using training EEG-fMRI connectivity data pairs, each pair comprising EEG connectivity data of a subject and fMRI connectivity data of the same subject; and
taking an action based on the predicted fMRI connectivity data.

Embodiment 2 is the method of embodiment 1, wherein:
the EEG connectivity data represents, for each pair of parcellations in a first set of parcellations, a correlation between brain activity of the pair of parcellations; and
the predicted fMRI connectivity data represents, for each pair of parcellations in a second set of parcellations, a correlation between brain activity of the pair of parcellations.

Embodiment 3 is the method of embodiment 2, wherein the first set of parcellations includes parcellations that are proximate to a surface of the brain of the particular subject.

Embodiment 4 is the method of any one of embodiments 2 or 3, wherein the first set of parcellations is smaller than the second set of parcellations.

Embodiment 5 is the method of any one of embodiments 1-4, wherein taking an action comprises using the predicted fMRI connectivity data as input to one or more machine learning models.

Embodiment 6 is the method of any one of embodiments 1-5, wherein taking an action comprises one or more of:
categorizing the particular subject as having a particular brain condition;
determining the particular subject as a candidate for neurosurgery;
automatically determining that the particular subject should undergo further testing for a particular brain condition; or
applying transcranial magnetic stimulation based at least in part on the predicted fMRI connectivity data.

Embodiment 7 is the method of any one of embodiments 1-6, wherein the EEG connectivity data comprises a plurality of channels corresponding to respective frequency bands of the raw EEG data.

Embodiment 8 is the method of embodiment 7, wherein generating the EEG connectivity data comprises performing Fourier decomposition on the raw EEG data.

Embodiment 9 is the method of any one of embodiments 1-8, wherein generating the EEG connectivity data comprises determining, for each of a plurality of electrodes of the specified montage, one or more corresponding parcellations.

Embodiment 10 is the method of any one of embodiments 1-9, wherein the generative neural network has been trained using adversarial learning.

Embodiment 11 is a system comprising one or more computers and one or more storage devices storing instructions that are operable, when executed by the one or more computers, to cause the one or more computers to perform the method of any one of embodiments 1-10.

Embodiment 12 is a computer storage medium encoded with a computer program, the program comprising instructions that are operable, when executed by data processing apparatus, to cause the data processing apparatus to perform the method of any one of embodiments 1-10.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain some cases, multitasking and parallel processing may be advantageous.

The invention claimed is:
1. A method comprising:
obtaining first connectivity data generated from raw brain data captured from a brain of a subject, wherein the first connectivity data represents, for each pair of parcellations in a first set of parcellations in the brain of the subject, a correlation between brain activity of the pair of parcellations;
processing the first connectivity data using a machine learning model to generate predicted second connectivity data, wherein:
the predicted second connectivity data represents, for each pair of parcellations in a second set of parcellations in the brain of the patient that is different from the first set of parcellations, a correlation between brain activity of the pair of parcellations,
the machine learning model having been trained to determine a mapping between correlation values for the first set of parcellations and correlation values for the second set of parcellations,
the first connectivity data is generated from EEG data captured from the brain of the subject, and the predicted second connectivity data represents predicted fMRI data,
the EEG data is captured from the brain of the subject using a particular EEG montage that identifies, for each of a plurality of EEG electrodes, a respective location on a scalp of the subject,
the EEG data comprises respective channel data captured by each of the plurality of EEG electrodes of the particular EEG montage, and
the first connectivity data is generated by performing operations comprising:
determining, for each parcellation in the first set of parcellations, a corresponding electrode of the plurality of electrodes of the particular EEG montage; and
determining, for each pair of parcellations in the first set of parcellations comprising a first parcellation and a second parcellation, a correlation between (i) the channel data captured by the electrode corresponding to the first parcellation and (ii) the channel data captured by the electrode corresponding to the second parcellation; and
taking an action based on the predicted second connectivity data.
2. The method of claim 1, the machine learning model having been trained using a plurality of training examples each corresponding to a respective second subject and each comprising (i) a training input representing correlations between brain activity of the first set of parcellations in the brain of the respective second subject and (ii) a target output representing correlations between brain activity of the second set of parcellations in the brain of the respective second subject.
3. The method of claim 2, wherein:
the first connectivity data has been generated from EEG data captured from the brain of the subject using a first EEG montage, and
for each of the plurality of training examples, the training input of the training examples has been generated from EEG data captured from the brain of the respective second subject using a respective second EEG montage that is different from the first EEG montage.

4. The method of claim 1, wherein the machine learning model is a generative neural network, the generative neural network having been trained using a generative adversarial network comprising a discriminator neural network, the training comprising:
processing a training first connectivity data using the generative neural network to generate training second connectivity data;
processing, by the discriminator neural network, the training second connectivity data to generate a prediction of whether the training second connectivity data is real connectivity data or synthetic connectivity data; and
determining a parameter update for the generative neural network according to an error of the prediction of the discriminator neural network.
5. The method of claim 4, wherein taking an action based on the predicted second connectivity data comprises performing anomaly detection on the first connectivity data, comprising:
processing the predicted second connectivity data using the discriminator neural network to generate a prediction of whether the predicted second connectivity data is real or synthetic;
determining whether the first connectivity data is anomalous according to an error of the prediction of the discriminator neural network exceeding a predetermined threshold; and
taking an action if determining that the first connectivity data is anomalous.
6. The method of claim 1, wherein the first set of parcellations includes parcellations that are proximate to a surface of the brain of the particular subject.
7. The method of claim 1, wherein the first set of parcellations includes fewer parcellations than the second set of parcellations.
8. The method of claim 1, wherein the first connectivity data comprises a plurality of channels corresponding to respective frequency bands of the EEG data.
9. The method of claim 1, wherein the first connectivity data has been generated from fMRI data captured from the brain of the subject, and the predicted second connectivity data represents predicted EEG data.
10. The method of claim 1, wherein taking an action comprises one or more of:
providing the predicted fMRI connectivity data as input to one or more other machine learning models;
categorizing the particular subject as having a particular brain condition;
determining the particular subject as a candidate for neurosurgery;
automatically determining that the particular subject should undergo further testing for a particular brain condition; or
applying transcranial magnetic stimulation based at least in part on the predicted fMRI connectivity data.
11. A system comprising one or more computers and one or more storage devices storing instructions that are operable, when executed by the one or more computers, to cause the one or more computers to perform operations comprising:
obtaining first connectivity data generated from raw brain data captured from a brain of a subject, wherein the first connectivity data represents, for each pair of parcellations in a first set of parcellations in the brain of the subject, a correlation between brain activity of the pair of parcellations;

processing the first connectivity data using a machine learning model to generate predicted second connectivity data, wherein:
the predicted second connectivity data represents, for each pair of parcellations in a second set of parcellations in the brain of the patient that is different from the first set of parcellations, a correlation between brain activity of the pair of parcellations,
the machine learning model having been trained to determine a mapping between correlation values for the first set of parcellations and correlation values for the second set of parcellations;
the first connectivity data is generated from EEG data captured from the brain of the subject, and the predicted second connectivity data represents predicted fMRI data,
the EEG data is captured from the brain of the subject using a particular EEG montage that identifies, for each of a plurality of EEG electrodes, a respective location on a scalp of the subject,
the EEG data comprises respective channel data captured by each of the plurality of EEG electrodes of the particular EEG montage, and
the first connectivity data is generated by performing operations comprising:
determining, for each parcellation in the first set of parcellations, a corresponding electrode of the plurality of electrodes of the particular EEG montage; and
determining, for each pair of parcellations in the first set of parcellations comprising a first parcellation and a second parcellation, a correlation between (i) the channel data captured by the electrode corresponding to the first parcellation and (ii) the channel data captured by the electrode corresponding to the second parcellation; and
taking an action based on the predicted second connectivity data.

12. The system of claim 11, the machine learning model having been trained using a plurality of training examples each corresponding to a respective second subject and each comprising (i) a training input representing correlations between brain activity of the first set of parcellations in the brain of the respective second subject and (ii) a target output representing correlations between brain activity of the second set of parcellations in the brain of the respective second subject.

13. The system of claim 11, wherein the machine learning model is a generative neural network, the generative neural network having been trained using a generative adversarial network comprising a discriminator neural network, the training comprising:
processing a training first connectivity data using the generative neural network to generate training second connectivity data;
processing, by the discriminator neural network, the training second connectivity data to generate a prediction of whether the training second connectivity data is real connectivity data or synthetic connectivity data; and
determining a parameter update for the generative neural network according to an error of the prediction of the discriminator neural network.

14. The system of claim 13, wherein taking an action based on the predicted second connectivity data comprises performing anomaly detection on the first connectivity data, comprising:
processing the predicted second connectivity data using the discriminator neural network to generate a prediction of whether the predicted second connectivity data is real or synthetic;
determining whether the first connectivity data is anomalous according to an error of the prediction of the discriminator neural network exceeding a predetermined threshold; and
taking an action if determining that the first connectivity data is anomalous.

15. One or more non-transitory storage media storing instructions that when executed by one or more computers cause the one or more computers to perform operations comprising:
obtaining first connectivity data generated from raw brain data captured from a brain of a subject, wherein the first connectivity data represents, for each pair of parcellations in a first set of parcellations in the brain of the subject, a correlation between brain activity of the pair of parcellations;
processing the first connectivity data using a machine learning model to generate predicted second connectivity data, wherein:
the predicted second connectivity data represents, for each pair of parcellations in a second set of parcellations in the brain of the patient that is different from the first set of parcellations, a correlation between brain activity of the pair of parcellations,
the machine learning model having been trained to determine a mapping between correlation values for the first set of parcellations and correlation values for the second set of parcellations;
the first connectivity data is generated from EEG data captured from the brain of the subject, and the predicted second connectivity data represents predicted fMRI data,
the EEG data is captured from the brain of the subject using a particular EEG montage that identifies, for each of a plurality of EEG electrodes, a respective location on a scalp of the subject,
the EEG data comprises respective channel data captured by each of the plurality of EEG electrodes of the particular EEG montage, and
the first connectivity data is generated by performing operations comprising:
determining, for each parcellation in the first set of parcellations, a corresponding electrode of the plurality of electrodes of the particular EEG montage; and
determining, for each pair of parcellations in the first set of parcellations comprising a first parcellation and a second parcellation, a correlation between (i) the channel data captured by the electrode corresponding to the first parcellation and (ii) the channel data captured by the electrode corresponding to the second parcellation; and
taking an action based on the predicted second connectivity data.

16. The non-transitory storage media of claim 15, the machine learning model having been trained using a plurality of training examples each corresponding to a respective second subject and each comprising (i) a training input representing correlations between brain activity of the first set of parcellations in the brain of the respective second subject and (ii) a target output representing correlations between brain activity of the second set of parcellations in the brain of the respective second subject.

17. The non-transitory storage media of claim 15, wherein the machine learning model is a generative neural network, the generative neural network having been trained using a generative adversarial network comprising a discriminator neural network, the training comprising:
- processing a training first connectivity data using the generative neural network to generate training second connectivity data;
- processing, by the discriminator neural network, the training second connectivity data to generate a prediction of whether the training second connectivity data is real connectivity data or synthetic connectivity data; and
- determining a parameter update for the generative neural network according to an error of the prediction of the discriminator neural network exceeding a predetermined threshold.

18. The non-transitory storage media of claim 17, wherein taking an action based on the predicted second connectivity data comprises performing anomaly detection on the first connectivity data, comprising:
- processing the predicted second connectivity data using the discriminator neural network to generate a prediction of whether the predicted second connectivity data is real or synthetic;
- determining whether the first connectivity data is anomalous according to an error of the prediction of the discriminator neural network exceeding a predetermined threshold; and
- taking an action if determining that the first connectivity data is anomalous.

* * * * *